(12) United States Patent
Cowan et al.

(10) Patent No.: US 7,894,910 B2
(45) Date of Patent: Feb. 22, 2011

(54) SYSTEMS AND METHODS FOR IMPLANTABLE LEADLESS COCHLEAR STIMULATION

(75) Inventors: Mark W. Cowan, Fremont, CA (US);
Richard E. Riley, Palo Alto, CA (US);
Axel F. Brisken, Fremont, CA (US);
Debra S. Echt, Woodside, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

(21) Appl. No.: 11/764,611

(22) Filed: Jun. 18, 2007

(65) Prior Publication Data

US 2007/0293913 A1 Dec. 20, 2007

Related U.S. Application Data

(60) Provisional application No. 60/805,323, filed on Jun. 20, 2006.

(51) Int. Cl.
*A61N 1/36* (2006.01)
(52) U.S. Cl. ....................................... 607/57
(58) Field of Classification Search .............. 607/55–57
See application file for complete search history.

(56) References Cited

U.S. PATENT DOCUMENTS

| 3,751,605 | A | 8/1973 | Michelson |
| 4,400,590 | A | 8/1983 | Michelson |
| 4,819,647 | A | 4/1989 | Byers et al. |
| 5,405,367 | A | 4/1995 | Schulman et al. |
| 6,037,704 | A | 3/2000 | Welle |
| 6,366,816 | B1 | 4/2002 | Marchesi |
| 6,671,559 | B2 | 12/2003 | Goldsmith et al. |
| 6,889,094 | B1 | 5/2005 | Kuzma et al. |
| 2004/0172083 | A1* | 9/2004 | Penner ........................ 607/35 |
| 2004/0230254 | A1* | 11/2004 | Harrison et al. ............... 607/57 |
| 2006/0136004 | A1* | 6/2006 | Cowan et al. ................. 607/33 |

FOREIGN PATENT DOCUMENTS

DE 4330680 3/1995

* cited by examiner

*Primary Examiner*—Eric D. Bertram
(74) *Attorney, Agent, or Firm*—Kilpatrick Townsend & Stockton LLP (57) ABSTRACT

Systems and methods are disclosed to enable hearing in the deaf by stimulating sites in the cochlea. The invention uses electrical stimulation in the cochlea, where vibrational energy from a source is received by an implanted device and converted to electrical energy and the converted electrical energy is used by implanted electrodes to stimulate the cochlear nerve. The vibrational energy is generated by a controller-transmitter, which could be located either externally or implanted. The vibrational energy is received by a receiver-stimulator, which contains multiple electrodes to stimulate along selected sites in the cochlea.

11 Claims, 6 Drawing Sheets

SYSTEMS AND METHODS FOR IMPLANTABLE LEADLESS COCHLEAR STIMULATION

CROSS-REFERENCES TO RELATED APPLICATIONS

The present application claims the benefit of provisional U.S. Application No. 60/805,323, filed Jun. 20, 2006, the full disclosure of which is incorporated herein by reference.

BACKGROUND OF THE INVENTION

1. Field of the Invention

The systems and methods of this invention relate to electrical stimulation of the cochlea of the ear and to cochlear nerves and to regions proximal to cochlear nerves of the ear as a treatment for hearing loss. Specifically, the present invention relates to methods and apparatus for applying such stimulation to selected regions of the cochlea without the use of leads of conventional cochlear implant systems.

2. Description of the Background Art

Electrical stimulation in the cochlea of the ear for the purpose of treating patients with hearing loss has been known and actively practiced for several decades. Application of an electrical field between electrodes in the cochlea stimulates cochlear nerve tissues and is known to effectively modify signal pathways to the brain to emulate the sensation of hearing sounds. These applications currently use several components including externally applied parts and implanted parts, collectively referred to as a cochlear implant system (CIS). A cochlear implant system consists of a microphone, which picks up sound from the environment; a sound-speech processor, which selects and arranges sounds picked up by the microphone; a transceiver-stimulator, which receives signals from the sound-speech processor and converts them into electric impulses; and electrodes, which collect the impulses from the transceiver-stimulator and applies them to the cochlea. As the cochlea is stimulated, signals are sent to the brain and interpreted by the brain as sound.

A CIS device does not restore or create normal hearing, nor does it amplify sound like a hearing aid. CIS provides a train of stimulation pulses that are correlated with sound and provides this interpreted pattern of impulses to the brain. The brain is capable of associating these substituted impulses as sound which enables the patient/brain to reform environmental sound recognition and speech recognition. Depending on the individual patient, cochlear stimulation can effectively activate signal pathways along the cochlear nerve, to the brain, and the brain associates these artificially induced impulses with sounds. For example, speech recognition can be accomplished in profoundly deaf patients who learn to associate these stimuli with sound, particularly in combination with reading lips. Treatment regimens and targeted cochlear nerve locations are known in related art through use of current, common stimulation devices and methods. Commonly implanted CIS devices for cochlear nerve stimulation are made by such companies as Med El Medical Electronics, Advanced Bionics, Cochlear Inc. and others.

Figure 1:
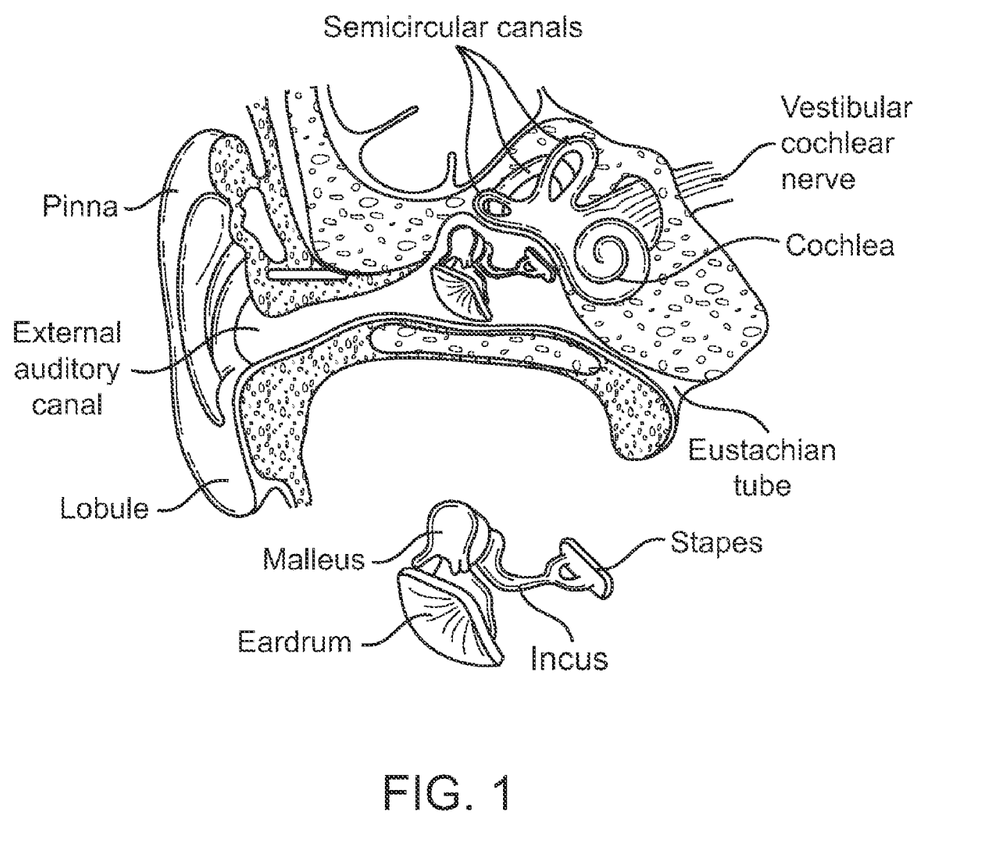
FIG. 1 is a schematic showing the basics of the ear/hearing anatomy.

As illustrated in FIG. 1, the hearing system is an anatomical structure that begins at the ear canal. Sound travels through the canal to the ear drum which vibrates and sets in motion bones in the inner ear. This motion causes the fluid in the cochlea to move small hair cells. The hair cells transduce this movement into electrical impulses in the cochlear nerve which sends the impulses to the brain, which then interprets the impulses as sound.

Figure 2A:
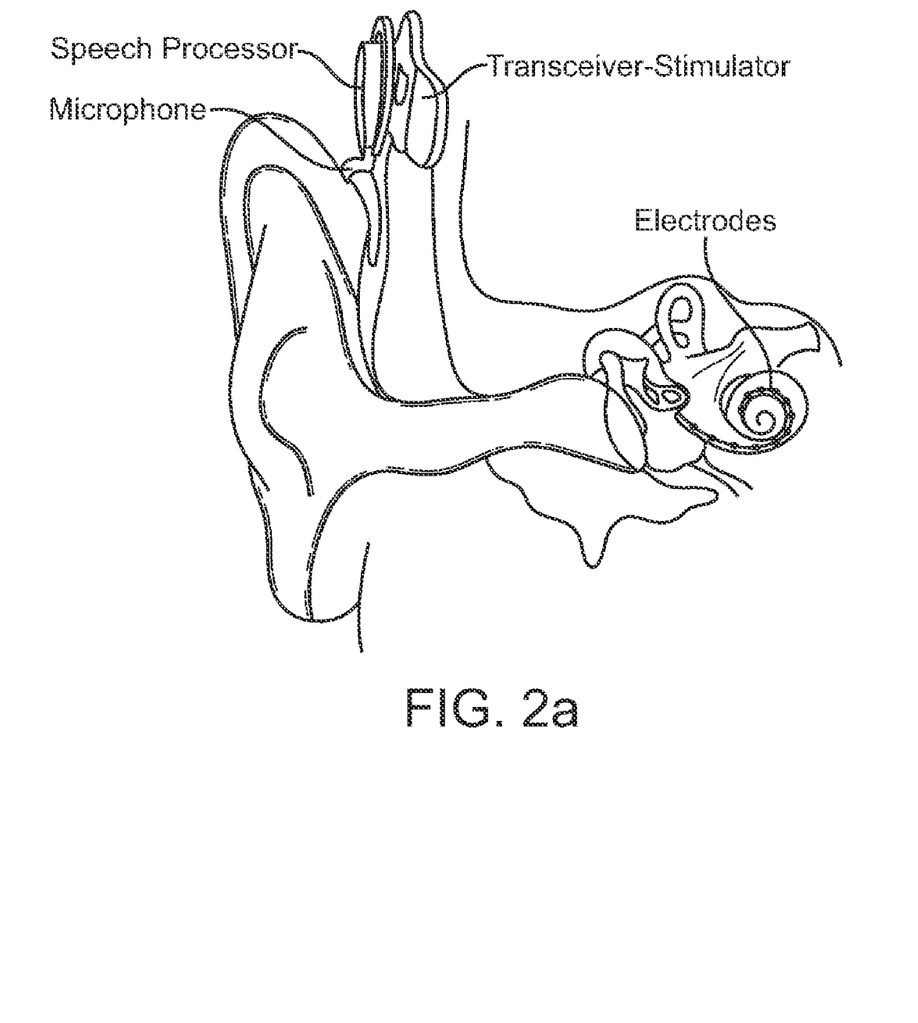
FIGS. 2a and 2b are schematics showing a typical cochlear implant system in application with an external microphone and sound-speech processor and an implantable transceiver-stimulator and electrodes for stimulation in the cochlea of the ear.

CIS is a well known medical treatment used primarily to restore speech recognition in the patients with conditions that prevent the hair cells in the cochlea from activating, particularly in the profoundly deaf. Use of the CIS components (microphone, sound-speech processor, transceiver-stimulator, and electrodes) for a conventional CIS device is illustrated in FIG. 2a. The Microphone is typically worn behind the ear and configured for wear to hook over the top of the ear or alternatively can be worn on the clothing or placed in a pocket. There is a direct connection from the Microphone, via a wire, to the Sound-speech processor. Alternative embodiments sometimes include the Microphone and the Sound-speech processor in the same device. The Sound-speech processor interprets the sound waves it receives and converts the frequency of the sound waves into trains of pulses with varying pulse durations. The series of pulses is then sent to the Transceiver-stimulator to be converted into electrical signals to be sent between electrodes that are positioned in the cochlea. This series of pulses is communicated from the Sound-speech processor either by direct wired connection to the Transceiver-stimulator or by radiofrequency communication between the two components. The Transceiver-stimulator is implanted subcutaneously between the patient's skin and skull and the Sound-speech processor may be mounted externally on the skull proximate to the Transceiver-stimulator. The Electrodes are connected to the Transceiver-stimulator via a lead that is tunneled from the cochlea to the Transceiver-stimulator. Electrodes are dispersed along the distal end of the lead and positioned throughout the cochlea so that a variety of locations in the cochlea can be stimulated independently. Prior art describes effective processes and algorithms to convert sound into impulse trains and to send those trains to electrodes in selected cochlea regions to stimulate the cochlear nerves.

Figure 2B:
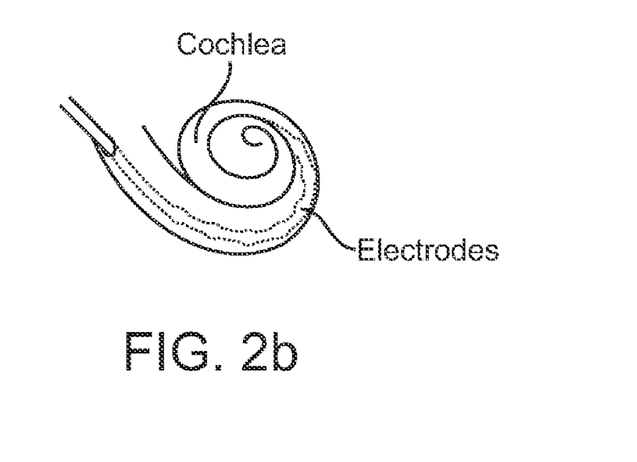

In CIS systems, electrical energy is delivered through lead wires to the electrodes. As shown in FIG. 2b, CIS implanted electrodes are positioned throughout the spiral structure of the cochlea in order to stimulate different regions in the cochlear nerve. CIS uses the implanted electrodes to deliver a variety of stimulation modalities along the cochlea and thus along the cochlear nerve with the electric pulse waveform defined by a plurality of variables, including but not limited to: pulse width or pulse frequency (Hz).

As described above, CIS devices are battery-powered electronic devices connected via insulated metal lead(s) to electrodes which are placed in the cochlea around or in close proximity to the cochlear nerve or cochlear nerve bundle. The implanted electrodes for CIS are positioned on leads that are placed percutaneously, through needle punctures or through direct surgical access to position the electrodes along the spiral shaped cochlea. A typical application may utilize 16 electrodes (for example, selected and used as 8 pairs of electrodes) positioned in regions that are targeted for electrical stimulation. The implanted leads are then subcutaneously tunneled to the Transceiver-stimulator (also referred to as a controller) that is implanted in a subcutaneous pocket between the skin and the skull. The use of these lead wires is associated with significant problems such as complications due to infection, lead failure, lead migration, and electrode/lead dislodgement. Application of electrodes to the cochlea can be difficult because of the need to locate electrodes for effective therapy. Additionally, the implanted Transceiver-stimulator must be in communication with the external Sound-speech processor. This requires that the implanted Transceiver-stimulator have a percutaneous connection to the Sound-speech processor or that an RF or magnetic coupling be maintained. A percutaneous connection is often a source for infection and wound control.

Other prior art in many stimulation applications has attempted to deal with the complications and limitations imposed by the use of electrical leads. For example, self-contained implantable microstimulators and remotely powered microstimulators have been described; however each approach suffers from some significant limitation. A self-contained microstimulator must incorporate a battery or some other power supply; this imposes constraints on size, device lifetime, available stimulation energy, or all three. Constant communication from the Speech Processor would be required with the microstimulator imposing further constraints on maintaining a constant communication between the two devices. Due to high use or high energy requirements of the therapeutic stimulation some CIS devices contain rechargeable batteries or are powered remotely with the RF coupling to the controller.

For non-percutaneous connection solutions, between the Sound-speech processor and the Transceiver-stimulator, CIS devices have previously utilized either radiofrequency (RF) or electromagnetic transformer power transmission. RF energy transmission, unless the transmitting and receiving antennae are placed in close proximity, suffers from inefficiency and limited safe power transfer capabilities, limiting its usefulness in applications where recharging or stimulation must be accomplished at any significant depth (>1-2 cm) within the body. Electromagnetic coupling can more efficiently transfer electrical power, and can safely transfer higher levels of power (devices with capacity in excess of 20 Watts have been produced) but again relies on close proximity between transmitting and receiving coils.

The methods and apparatus of the current invention utilize vibrational energy, particularly at ultrasonic frequencies, to overcome many of the limitations of currently known solutions for cochlea stimulation, by achieving a cochlea stimulation capability without direct connection to the Sound-speech processor or without the use of leads connected to a controller.

The following patents, all of which are incorporated in this disclosure in their entirety, describe various aspects of using electrical stimulation for achieving various beneficial effects by cochlear implant systems. U.S. Pat. No. 3,751,605 titled "Method for Inducing Hearing" by Michelson describes methods for inducing the sensation of intelligible hearing by direct electrical excitation of the auditory nerve endings distributed along the basilar membrane within the cochlea. U.S. Pat. No. 4,400,590 titled "Apparatus for multichannel cochlear implant hearing aid system" by Michelson describes an intra-cochlear electrode array for electrically stimulating predetermined locations of the auditory nerve within the cochlea of the ear. U.S. Pat. No. 4,819,647 titled "Intracochlear electrode array" by Byers et al. also describes an intra-cochlear electrode array for electrically stimulating the cochlea of the ear. U.S. Pat. No. 6,671,559 titled "Transcanal, transtympanic cochlear implant system for the rehabilitation of deafness and tinnitus" by Goldsmith et al. describes an implantable application for cochlea stimulation using a system that couples communication and energy via RF or inductive coupling. U.S. Pat. No. 6,889,094 titled "Electrode array for hybrid cochlear stimulator" by Kuzma describes an implantable cochlear electrode array. U.S. Pat. No. 5,405,367 titled "Structure and Method of Manufacture of an Implantable Microstimulator" by Schulman et al. describes an implantable microstimulator used generally for stimulation of tissue. U.S. Pat. No. 6,037,704 titled "Ultrasonic Power Communication System" by Welle describes the use of ultrasound energy transfer from a transmitter to a receiver for purposes of powering a sensor or actuator without being connected by a lead/wire. U.S. Pat. No. 6,366,816 titled "Electronic Stimulation Equipment with Wireless Satellite Units" by Marchesi describes a tissue stimulation system based on a wireless radio transmission requiring the charging of a battery at the receiver and separate command signals used to control the delivery of stimulation. German patent application DE4330680A1 titled "Device for Electrical Stimulation of Cells within a Living Human or Animal" by Zwicker describes a general approach to power transfer using acoustic energy for tissue stimulation.

BRIEF SUMMARY OF THE INVENTION

This invention relates to methods and devices for using electrical stimulation in the cochlea of the ear as a treatment for hearing loss, effectively modifying signal pathways along the cochlear nerve, to the brain, to provide a functional capability of hearing, particularly for environmental sound recognition and speech recognition. This invention uses vibrational energy as a means to transmit energy and signal information from a first device, to a second device containing means to receive such vibrational energy and converting it into electrical energy and then apply that electrical energy to stimulating electrodes. The first device is intended to be either implanted or to be used externally. The second device is intended to be either permanently or temporarily implanted with stimulating electrodes in the cochlea of the ear.

This application of electrical stimulation is to specifically eliminate one or more direct lead connections between the components of a Cochlear Implant System. The invention is a system comprising a microphone, a sound-speech processor, a controller-transmitter, and an implanted receiver-stimulator with stimulation electrodes, such that the stimulation electrodes would be implanted in the cochlea of the ear, in close proximity to the cochlear nerve or cochlear nerve bundle to be stimulated to facilitate a sensation of sound in the brain. Systems incorporating the concepts presented herein are advantageous with respect to currently available devices, particularly by eliminating the requirement for leads connecting components of conventional CIS systems, and by providing the capability for simultaneous or sequenced stimulation of multiple sites.

In one preferred embodiment, the controller-transmitter is applied on the external surface of the skin. In another embodiment, the controller-transmitter is implanted subcutaneously beneath the skin. The receiver-stimulator is implanted such that electrodes of the receiver-stimulator are within the cochlea of the ear. In one embodiment of the receiver-stimulator, the receiver-stimulator is positioned at one implantation site and connected to the electrodes in the cochlea via a lead. In another embodiment of the receiver-stimulator, the receiver-stimulator is adapted to be implanted within the cochlea and multiple electrodes are dispersed on the device throughout the cochlea. In yet another embodiment of the receiver-stimulator, the receiver-stimulator is miniaturized to contain a pair of electrodes and multiple receiver-stimulator devices are individually positioned within the cochlea. The transmitted vibrational energy is directed to the receiver-stimulator to cause electrical stimulation at the electrodes of the receiver-stimulator.

In the implanted embodiment of the controller-transmitter, the sound-speech processor communicates with the controller-transmitter via RF, electromagnetic or acoustic coupling. In the external embodiment of the controller-transmitter, the controller-transmitter may be directly connected to the sound-speech processor or be incorporated with the sound-speech processor into a single device. The acoustic energy from the external controller-transmitter is coupled through the skin as well as any underlying tissues, to the implanted receiver-stimulator device. The external controller-transmitter is under control of the sound-speech processor. Thus, when the microphone picks up sound, the sound-speech processor converts the sound into associated stimulation characteristics, for example the frequency or pulse duration of the stimulating waveform or selected electrodes in specific regions within the cochlea, the stimulation characteristics are communicated to the controller-transmitter and vibrational energy is transmitted to the receiver-stimulators. This process enables the system to convert sound into stimulation impulses in the cochlea without direct connections the electrodes.

DETAILED DESCRIPTION OF THE INVENTION

The systems and devices described here comprise a controller-transmitter device that will deliver vibrational energy and information to one or more implanted receiver-stimulator device(s) that will convert the vibrational energy to electrical energy of a form that can be used to electrically stimulate cochlear nerves. The vibrational energy can be applied with ultrasound as a single burst or as multiple bursts or as a continuous wave with appropriate selection of the following parameters:

| Parameter | Value Range |
| --- | --- |
| Ultrasound frequency | 20 kHz-10 MHz |
| Burst Length (#cycles) | 3-Continuous |
| Stimulation Pulse Duration | 0.1 μsec-Continuous |
| Duty Cycle | 0-100% |
| Mechanical Index | $\leq 1.9$ |

The controller-transmitter device would contain one or more ultrasound transducers of appropriate size(s) and aperture(s) to generate sufficient acoustic power to achieve the desired stimulation at the location of an implanted receiver-stimulator device. Additionally, multiple implanted receiver-stimulator devices may be placed within the region insonified by the controller-transmitter device. Multiple receiver-stimulator implants may function simultaneously; and, it is possible for multiple devices to function independently, either by responding only to a specific transmitted frequency, or through the use of a selective modulation technique such as pulse width modulation, or through encoding techniques such as time-division multiplexing.

A receiver-stimulator would be placed percutaneously or surgically. Utilizing a percutaneous needle delivery technique to access the cochlea, a miniaturized receiver-stimulator device disposed within the delivery needle is implanted into the cochlea. Various techniques and tools for surgical access and probing of the cochlea that are currently used, or have been described in the literature, could be adapted to facilitate delivery of the receiver-stimulator to these locations; the receiver-transmitter may incorporate means to provide permanent attachment to the implant site including possibly helical coils, barbs, tines, or the like or would be adapted in form to expand/spring against the tissue to maintain its position.

Functionally, the receiver-stimulator device comprises an ultrasound transducer to receive acoustic energy and transform it into electrical energy, an electrical circuit to transform the alternating electrical energy into a direct current, and electrodes to transfer the electrical field energy between an electrode pair to the cochlea.

Additionally, a controller-transmitter device is adapted for directional, vibrational energy transmission emitted by the device to intersect the implanted receiver-stimulator. In an external version of the controller-transmitter, the transducer portion of the transmitter would be placed over the skin directionally angled to the target region containing the receiver-stimulator with acoustic gel, or other means, used for coupling the acoustic energy to the skin. In an implanted version, the controller-transmitter device containing the transmitting transducer is implanted typically just beneath the skin in a subcutaneous space.

The controller-transmitter device would contain elements similar to most currently available CIS systems, including a power source, stimulation control and timing circuitry. In its external embodiment, it would be possible to integrate the function of a sound-speech processor into a single enclosure with the controller-transmitter, or still yet integrate the function of the microphone, the sound-speech processor, and the controller transmitter into a single enclosure. In its implantable embodiment, the controller-transmitter would communicate with an outside sound-speech processor component via RF, electromagnetic, or acoustic means for data transmission of device function. Additionally, the controller-transmitter device would contain an ultrasound amplifier and one or more ultrasound transducers to generate acoustic energy, and transmit such energy in the general direction of the receiver-stimulator implanted in the body. The duration, timing, and power of the acoustic energy transmission would be controlled as required, per sound-speech processing parameters that are constructed for specific sound sensations.

A single receiver-stimulator device is implanted with the electrodes positioned within the cochlea of the ear. The single receiver-stimulator device may be adapted to contain multiple electrodes dispersed through the cochlea. Alternatively, it would be possible to implant a plurality of miniaturized receiver-stimulator devices throughout the cochlea to stimulate either simultaneously by receiving the same transmitted acoustic energy or independently by responding only to acoustic energy of a specific character (i.e., of a certain frequency, amplitude, or by other modulation or encoding of the acoustic waveform) intended to energize only that specific device. This enables a much more robust utilization of site and region specific stimulation not currently practical with current lead-based implementations whose electrode spacing is fixed on the lead set selected for use and may not adapt itself to the structure of the cochlea. Selecting multiple sites and regions for treatments would be greatly enhanced by eliminating the need to connect multiple electrode sites to the stimulation energy source by anticipating the required spacing between electrodes.

These examples are representative and in no way limiting the applications in which a stimulator based on using vibrational energy may be utilized in this invention to stimulate within the cochlea of the ear to treat provide a sound sensation to the brain.

The delivery of ultrasound energy and, therefore, electrical stimulation would be automatically triggered based on sound information received through a microphone and through a sound-speech processor. More specifically, the timing of the initiation of the delivery and/or the duration of the delivery and/or the energy content of the delivery and/or the information content of the delivery would be based upon processing sound picked up through this CIS system.

Figure 3A:
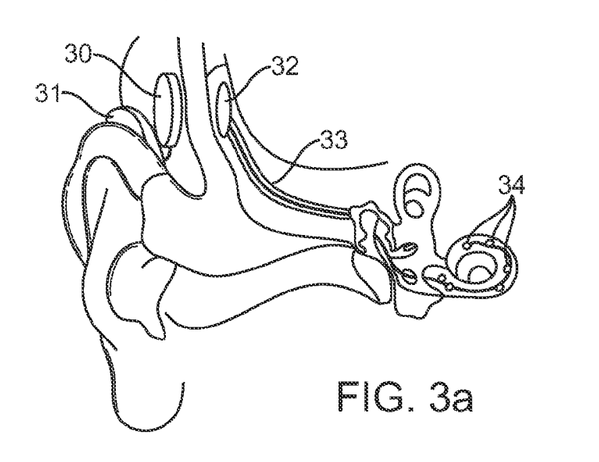
FIGS. 3a, 3b, and 3c are schematics showing the leadless stimulation system of the present invention with an externally applied acoustic transmitter-controller and implanted receiver-stimulators for stimulation in the cochlea of the ear.
Figure 3B:
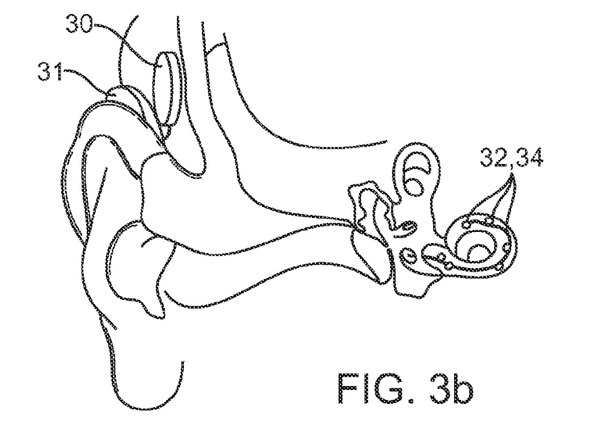
Figure 3C:
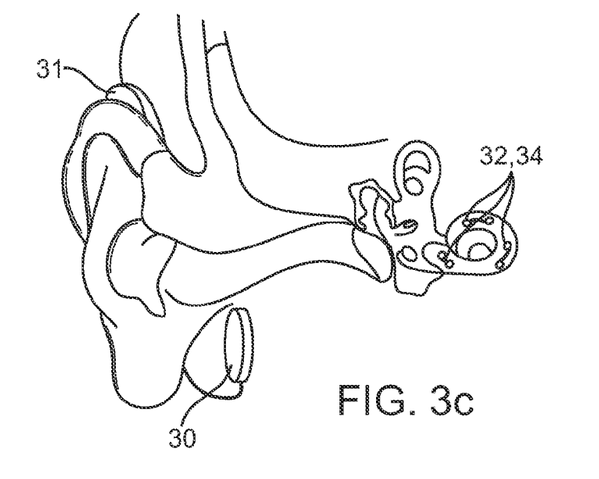

Examples of such an acoustic CIS system as a cochlea stimulator are illustrated in FIGS. 3a-3c.

In FIG. 3a, a sound processing device 31 containing a sound microphone, amplifier, sound processing circuitry, ultrasound amplifier, and battery circuitry to receive ambient sound is shown mounted over the ear. The sound processing device 31 is connected via a lead/cable to one or more controller-transmitter transducers 30, shown here mounted to the outside surface of the skull, on the scalp. It should be appreciated that the functional components of the sound processor and controller-transmitter could be partitioned as desired into one or more enclosures with the important function of the acoustic energy transfer being applied through a transmission transducer directly to the external surface of the body. A receiver-stimulator consisting of a receiver 32, a lead connection 33, and electrodes 34 is implanted in the body. The receiver 32 is situated such that the directional angle of the transmitted ultrasound beam from the controller-transmitter transducer 30 would intersect the receiver 32. An ultrasound signal is transmitted by controller-transmitter transducer 30 through intervening tissue to the receiver 32 containing means to receive this acoustic energy and convert it into an electrical waveform which may then be applied to the attached electrodes. The sound processing circuitry of sound processing device 31 would separate the sound into multiple channels associated with the multiple electrodes 34 implanted in the cochlea; the multiple channels of information would then be encoded into the transmitted ultrasound signal through an appropriate modulation technique. Thus, the transmitted modulated ultrasound signal will comprise an energy component to provide power to the implanted circuitry and an information component to provide signal content to multiple electrodes. Implanted receiver 32 contains both an ultrasound receiving transducer and the necessary electronics circuitry to convert the acoustic energy into electrical power, to demodulate the signal content within the ultrasound signal into one or multiple signal channels, and one or multiple circuits to process the signal content and apply the product to the electrodes 34, which are disposed on an implantable lead 33, whose distal end is placed within the cochlea.

In FIG. 3b, an alternative embodiment of the present invention is illustrated. In FIG. 3b, sound processing device 31 containing a sound microphone, amplifier, sound processing circuitry, ultrasound amplifier, and battery circuitry to receive ambient sound is shown mounted over the ear. The sound processing device 31 is connected via a lead/cable to one or more controller-transmitter transducers 30, shown here mounted to the outside surface of the skull, on the scalp. A receiver-stimulator consisting of a receiver 32 and electrodes 34 is implanted fully within the cochlea. The receiver 32 is situated such that the directional angle of the transmitted ultrasound beam from the controller-transmitter transducer 30 would intersect the receiver 32. An ultrasound signal is transmitted by controller-transmitter transducer 30 through intervening tissue to the receiver 32 containing means to receive this acoustic energy and convert it into an electrical waveform which may then be applied to the attached electrodes. The sound processing circuitry of sound processing device 31 would separate the sound into multiple channels associated with the multiple electrodes 34 implanted in the cochlea; the multiple channels of information would then be encoded into the transmitted ultrasound signal through an appropriate modulation technique. Thus, the transmitted modulated ultrasound signal will comprise an energy component to provide power to the implanted circuitry and an information component to provide signal content to multiple electrodes. Implanted receiver 32 contains both an ultrasound receiving transducer and the necessary electronic circuitry to convert the acoustic energy into electrical power, to demodulate the signal content within the ultrasound signal into one or multiple signal channels, and one or multiple circuits to process the signal content and apply the output to the electrodes 34 which are disposed on receiver-stimulator, where the entirety of the receiver-stimulator is disposed within the cochlea.

In FIG. 3c, an alternative embodiment of the present invention is illustrated. In FIG. 3c, a sound processing device 31 containing a sound microphone, amplifier, sound processing circuitry, ultrasound amplifier, and battery circuitry to receive ambient sound is shown mounted over the ear. The sound processing device 31 is connected via a lead/cable to one or more controller-transmitter transducers 30, shown here mounted to the outside surface of the head, beneath the ear. It should be appreciated that the functional components of the sound processor and controller-transmitter could be partitioned as desired into one or more enclosures with the important function of the acoustic energy transfer being applied through a transmission transducer directly to the external surface of the body. Multiple receiver-stimulators consisting of a receiver 32 and electrodes 34 are implanted in the cochlea. The individual receiver-stimulators are situated such that the directional angle of the transmitted ultrasound beam from the controller-transmitter transducer 30 would intersect the multiple receivers 32. An ultrasound signal is transmitted by controller-transmitter transducer 30 through intervening tissue to the receivers 32 containing means to receive this acoustic energy and convert it into an electrical waveform which may then be applied to the attached electrodes. The sound processing circuitry of sound processing device 31 would separate the sound into multiple channels associated with the multiple receivers 32 implanted in the cochlea; the multiple channels of information would then be encoded into the transmitted ultrasound signal through an appropriate modulation technique. Thus, the transmitted modulated ultrasound signal will comprise an energy part to provide power to the implanted circuitry and an information part to provide signal content to multiple receivers. Implanted receiver 32 contains both an ultrasound receiving transducer and the necessary electronic circuitry to convert the acoustic energy into electrical power, to demodulate the signal content within the ultrasound signal into one or multiple signal channels, and one or multiple circuits to process the signal content and apply the product to the electrodes 34 which are disposed on the individual receiver-stimulator, each of the receiver-stimulators disposed within the cochlea It can be appreciated form FIGS. 3a, 3b, and 3c that alternatively (not shown) a controller-transmitter could be implanted in a subcutaneous space and that the sound processing system would communicate via RF, electromagnetic, or acoustic means to initiate ultrasound transmission from the controller-transmitter to the receiver-stimulator.

Figure 4A:
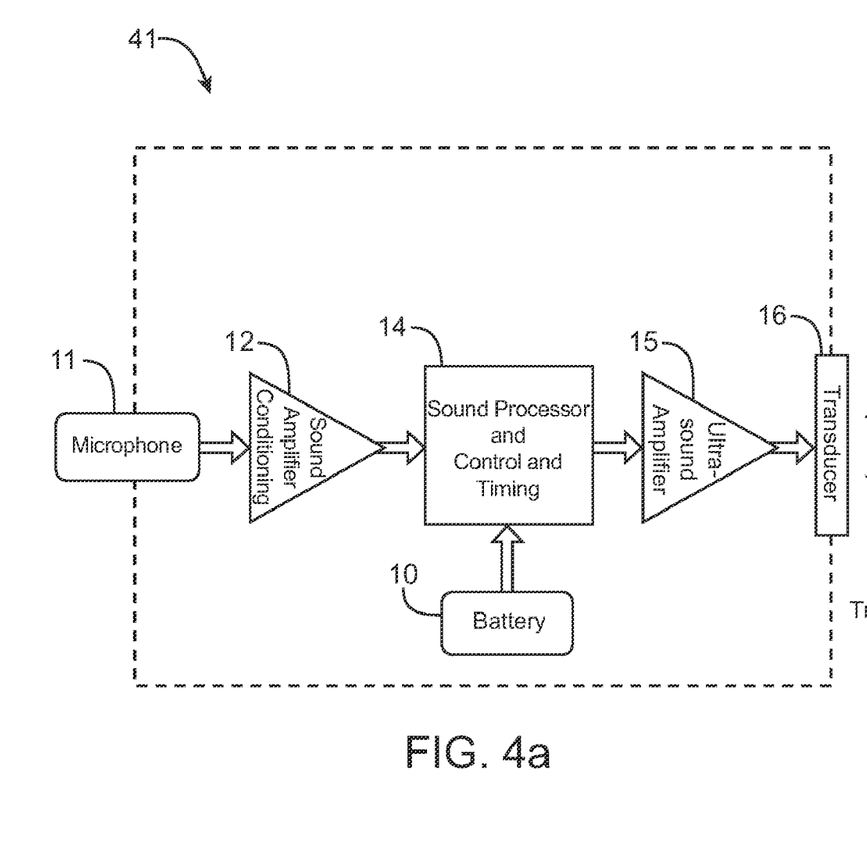
FIGS. 4a and 4b are block diagrams showing the components of the acoustic transmitter-controller and acoustic receiver-stimulators of the present invention.
Figure 4B:
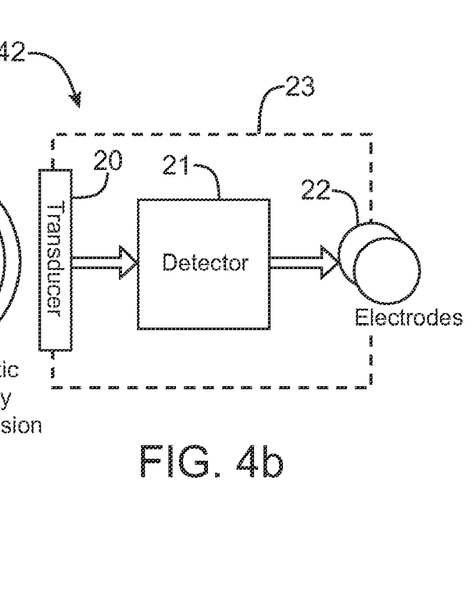

FIGS. 4a and 4b show more functional details of the system described above and shown in FIGS. 3a-3c. In FIG. 4a the sound processing and controller-transmitter device 41 comprises: a battery 10, a microphone 11, sound amplifier and conditioning circuitry 12, a sound processor and control and timing module 14, an ultrasound amplifier 15, and an ultrasound transducer 16. The battery 10 which provides power for the sound processing and controller-transmitter device may be of a type commonly used in CIS devices such as a lithium iodine cell or which is optionally a rechargeable battery. The microphone 11 is used to detect ambient sound. Sound pick-up is connected to sound amplifier and conditioning circuitry 12 and used by the circuitry to adjust delivery of stimulation. Sound characteristics would be processed into an associated stimulation therapy by the sound processor and control and timing module 14. Device parameters would include adjustments to transmission frequency, power amplitude, pulse duration, duty cycle, electrode selection, and the like in order to correlate ambient sound into a stimulation therapy. The sound processor and control and timing module 14 uses device parameters in conjunction with the acquired sound to generate the required control signals for the ultrasound amplifier 15 which in turn applies electrical energy to the ultrasound transducer 16 which in turn produces the desired acoustic beam. Ultrasound transducer 16 is made of piezoelectric ceramic material, a piezoelectric single crystal, or piezoelectric polymer or copolymer films suitable for generating sufficient acoustic energy. The controller-transmitter device 41 is enclosed in case 17. It should be appreciated that the functional elements of the sound processing and controller-transmitter device 41 could be encased in multiple enclosures and connected appropriately with direct wire connections or through communication via RF, electromagnetic, or acoustic signaling.

Figure 5:
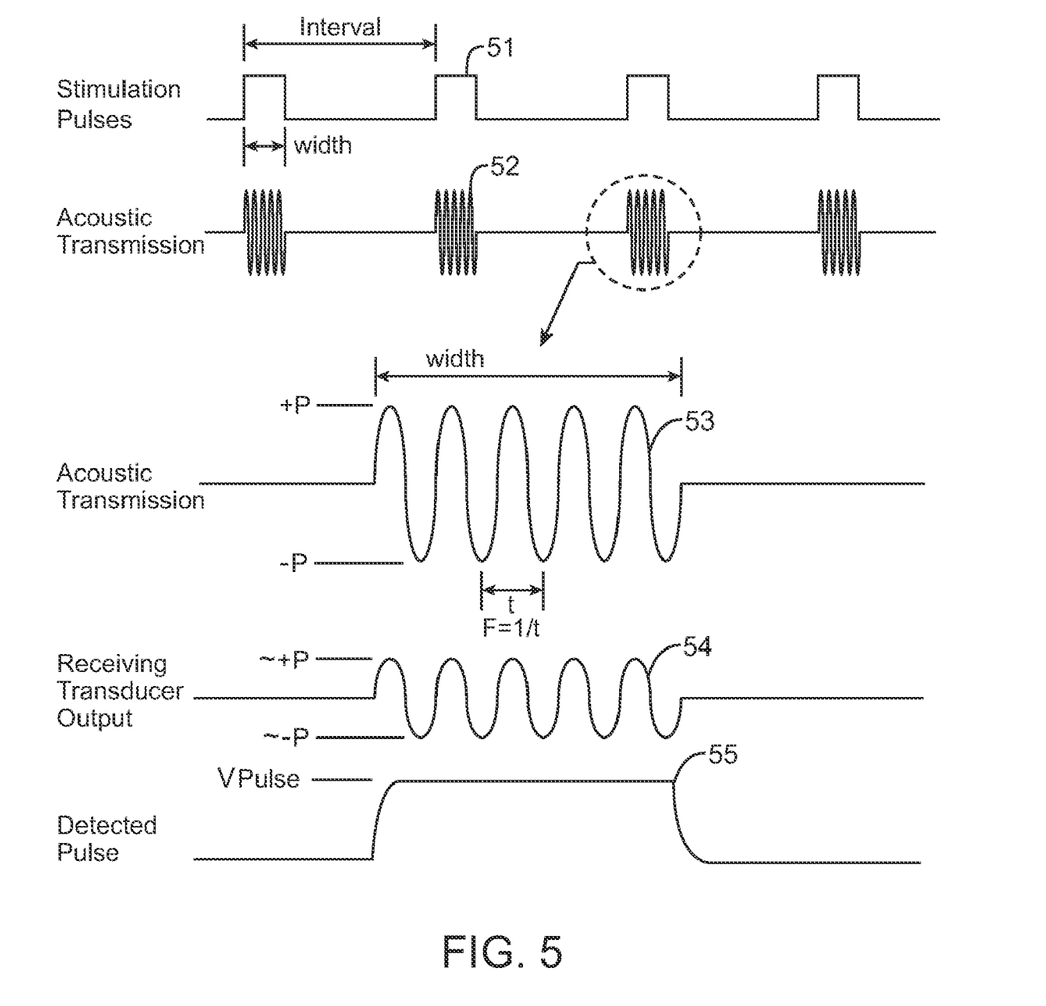
FIG. 5 illustrates representative acoustic and electrical signals useful in the systems and methods of the present invention.

Referring to FIG. 4b, the receiver-stimulator device 42, implanted in the path of the acoustic beam, contains an ultrasound transducer 20, an electrical circuit 21, and electrodes 22. Ultrasound transducer 20, typically made of a piezoelectric ceramic material, a piezoelectric single crystal, or piezoelectric polymer or copolymer films, intercepts a portion of the transmitted acoustic energy and converts it into an electrical current waveform from the original alternating nature of the applied ultrasound pressure wave. This electrical signal is applied to an electrical circuit 21 which may be one of a type commonly known as an envelope detector, and which may have one of many known circuit configurations, for example a full-wave rectifier, a half-wave rectifier, a voltage doubler or the like. Electrical circuit 21 produces a voltage pulse with amplitude proportional to the amplitude of the transmitted ultrasound burst and with a pulse length generally equal to the length of the transmitted burst. The circuit 21 may also be of different configurations and function, and provide output signals having characteristics other than a pulse. This signal is then applied to electrodes 22, which are typically made of platinum, platinum-iridium, gold, or the like. These may be incorporated onto the outer surface of the device and thus in direct contact within the cochlea. Alternatively, the electrodes 22 are connected via wires/leads to a main body that consists of the transducer 20 and electrical circuit 21 and the electrodes 22 are adapted to be shapeable, malleable configurations that conform to the structure of the cochlea. Electrodes may be adapted that are round, long, segmented, etc. to increase surface area or to control current density at the electrode. Electrodes may be placed along portions of the cochlea in linear alignment with the cochlea or in any arrangement suitable for the size and location of the regions of the cochlea targeted as a stimulation site. The receiver-stimulator device 42 is also enclosed within a sealed case 23 of biologically compatible material Referring also to previously described FIGS. 4a and 4b, FIG. 5 provides detail representing example acoustic and electrical signals of the present system. FIG. 5 first depicts a train of electrical stimulation pulses 51 which have a desired width and are repeated at a desired interval. The controller-transmitter device 41 produces acoustic transmissions 52, for the desired stimulation pulse width and repeated at the desired stimulation pulse interval, which are emitted from the ultrasound transducer 16. Below the waveform 52 is shown an enlargement 53 of a single acoustic burst. This burst again has a desired width, a desired oscillation frequency $F=1/t$, and also a desired acoustic pressure indicated by the peak positive pressure P+ and peak negative pressure P−. The acoustic pressure wave, when striking the receiving transducer 20 of the receiver-stimulator device 42 generates an electrical signal 54 having frequency and burst length matching that of the transmitted waveform 53 and amplitude proportional to the transmitted acoustic pressure ($\sim+/-P$). This electrical waveform is then rectified and filtered by the circuit 21 producing the desired pulse 55 with length equal to the burst length of the transmitted waveform 53 and amplitude (VPULSE) proportional to the amplitude of the electrical signal 54. Thus, it can be seen that it is possible in this example to vary the stimulation rate by varying the time between ultrasound bursts, to vary the duration of any one stimulation pulse by varying the duration of the ultrasound burst, and to vary the amplitude of the stimulation pulse by varying the amplitude of the transmitted ultrasound waveform. Circuit 21 could be configured to produce a direct current (DC) output or an alternating current (AC) output, or an output with any arbitrary waveform. Varying the use of signal information within the ultrasound transmission for pulse duration, pulse amplitude, and duty cycle would result in any type of burst sequencing or continuous delivery waveform effective for cochlear nerve stimulation. Using signal information in the ultrasound transmission the resultant waveshape may be a square wave, triangle wave, biphasic wave, multi-phase wave, or the like.

In practice, the amount of acoustic energy received by the implanted receiver-stimulator device will vary with ultrasound attenuation caused by loss in the intervening tissue, with spatial location of the receiver of the receiver-stimulator device with respect to the transmitted ultrasound beam as such a beam is typically non-uniform from edge-to-edge, and possibly with orientation (rotation) of the receiver-stimulator device with respect to the first. Such variation would affect the amplitude of the stimulating pulse for a given ultrasound transmit power (acoustic pressure amplitude). This limitation can be overcome by adjusting the ultrasound transmit power until the resultant stimulation waveform is consistent, a technique similar to that used currently to determine stimulation thresholds at the time of cardiac pacemaker implantation. Another approach would be to adjust automatically using sensing and logic within the first device. The first device would periodically sense the electrical output of the receiver-stimulator device and adjust power transmission accordingly to compensate for any change in the system including relative movement between the transmitting and receiving devices. Yet another embodiment for overcoming this limitation is where the transducer incorporated into the receiver-stimulator device is omni-directional in its reception capability. For example, to improve omni-directional sensitivity, the transducer may be spherical in shape or have specific dimensional characteristics relative to the wavelength of the transmitted ultrasound. Alternatively, multiple transducers are disposed at appropriate angles to reduce or eliminate the directional sensitivity of the device.

Figure 6A:
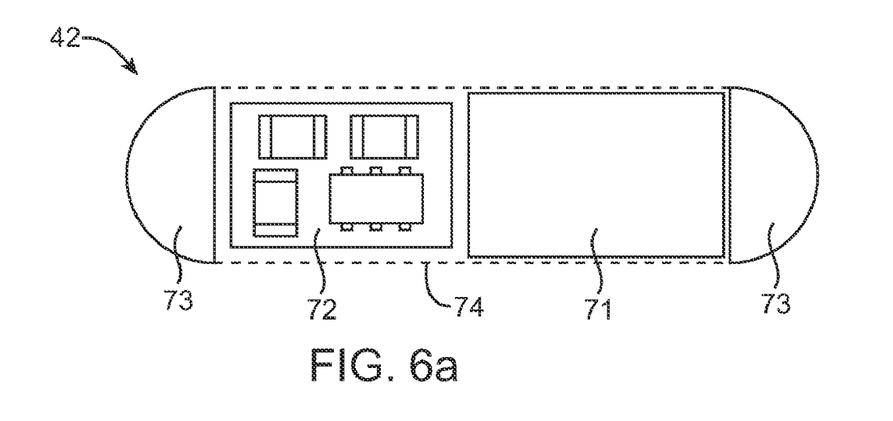
FIGS. 6a, 6b, and 6c are schematic illustrations showing components of the receiver-stimulator of the present invention.
Figure 6B:
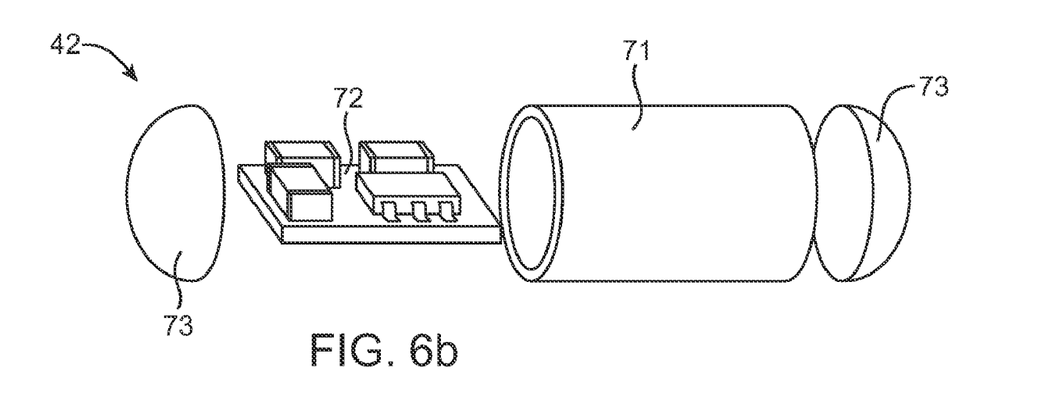

Referring also to previously described FIGS. 4a and 4b, FIGS. 6a through 6c illustrate two embodiments of a miniature implantable receiver-stimulator of a cylindrical profile, suitable perhaps for placement by stylet or by percutaneous injection through a hypodermic needle. FIG. 6a shows in plan view and 6b in perspective view such a receiver-stimulator 42 having a hollow, cylindrical ultrasound transducer 71, a circuit assembly 72 comprising the detector, and two electrodes 73 at either end of the assembly. It can be appreciated that any number of electrodes may be adapted to this embodiment. The transducer 71 would be made of an appropriate piezoelectric ceramic material, having two electrical activity contacts deposited on the outer and inner surfaces of the cylinder, respectively. The transducer and circuit would be encapsulated in an electrically insulating but acoustically transparent medium 74. The transducer 71 would be of a rigid piezoelectric material, typically a piezo-ceramic with electrodes deposited on the outer and inner surfaces of the cylinder. The circuit assembly 72 may be fabricated using known surface-mount or hybrid assembly techniques, upon either a fiberglass or ceramic substrate. Stimulation electrodes 73 would be fabricated of material commonly used in implanted electrodes, such as platinum, platinum-iridium, or the like. Necessary electrical wiring between the transducer, circuit board, and electrodes is not shown in these drawings. Typical dimensions of such a device would be 0.8 cm in length and 1.5 mm in diameter, and preferably smaller. Multiple electrodes could be adapted as appendages to the embodiment (not shown) or incorporated into fixation elements such as helical screws or barbs (not shown).

Figure 6C:
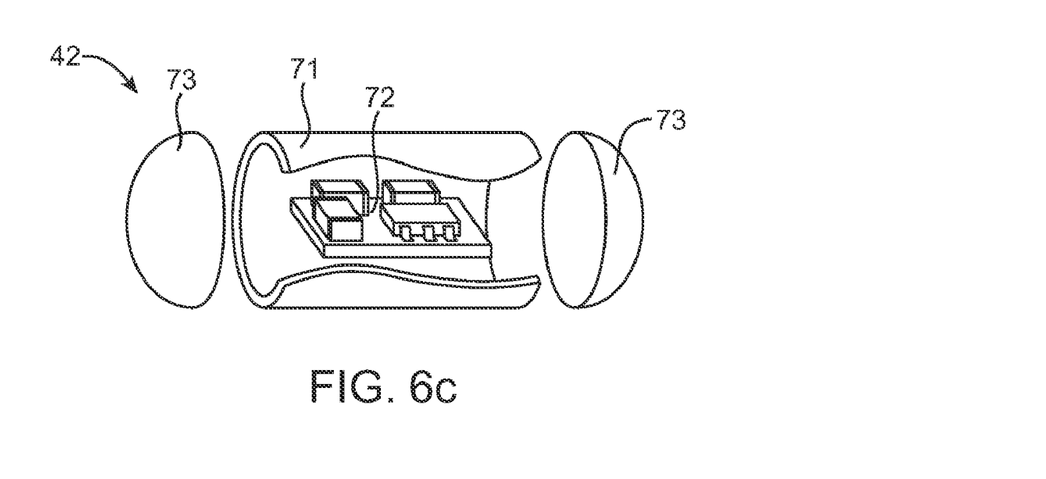

As shown in FIG. 6c, by using hybrid circuit techniques it may be possible to further miniaturize the circuit assembly 72 such that it would fit inside the hollow interior of the transducer 71. This would have the benefit of substantially reducing the length of the finished device.

While exemplary embodiments have been shown and described in detail for purposes of clarity, it will be clear to those of ordinary skill in the art from a reading of the disclosure that various changes in form or detail, modifications, or other alterations to the invention as described may be made without departing from the true scope of the invention in the appended claims. For example, while specific dimensions and materials for the device have been described, it should be appreciated that changes to the dimensions or the specific materials comprising the device will not detract from the inventive concept. Accordingly, all such changes, modifications, and alterations should be seen as within the scope of the disclosure.

What is claimed is:

1. A system for cochlea stimulation comprising:
    a sound-speech processor configured to convert sound into one or more stimulation characteristics;
    an implantable acoustic controller-transmitter configured to receive the one or more stimulation characteristics from the sound-speech processor and generate acoustic energy according to the received stimulation characteristics; and
    an implantable acoustic receiver-stimulator comprising a stimulation electrode assembly adapted to be in direct contact with the cochlea, wherein the receiver-stimulator is configured to receive and convert the acoustic energy into an electrical stimulation output delivered to the cochlea by the stimulation electrode assembly;
    wherein the controller-transmitter is configured to periodically sense the electrical stimulation output of the receiver-stimulator and adjust acoustic energy transmission accordingly in order to compensate for changes in the electrical stimulation output of the receiver-stimulator.

2. A system of claim 1, wherein the receiver-stimulator comprises an acoustic receiver which receives acoustic energy and generates alternating current, means for converting the alternating current to a pre-determined waveform, and stimulation electrodes adapted to deliver the pre-determined waveform to stimulate the cochlea.

3. A system of claim 1, wherein the controller-transmitter comprises a power source, control and timing circuitry to provide a stimulation signal, means for converting the stimulation signal to an acoustic energy signal, and means for transmitting the acoustic energy signal to the receiver-stimulator.

4. A system of claim 3, further comprising two or more receiver-stimulator device.

5. A system of claim 4, wherein the system is programmed to activate the receiver stimulator devices sequentially.

6. A system of claim 4, wherein the system is programmed to activate the receiver-stimulator devices simultaneously.

7. A system as in claim 3, wherein the controller-transmitter comprises a housing and wherein the power source, control and timing circuitry, means for converting the stimulation signal to an acoustic energy signal, and means for transmitting the acoustic energy signal to the receiver-stimulator are disposed at least partly within the housing.

8. A system as in claim 1, wherein the sound-speech processor comprises a sound microphone, an amplifier, sound processing circuitry, and battery circuitry.

9. A system as in claim 1, wherein the controller-transmitter and the sound-speech processor communicate using radiofrequency signals.

10. A system as in claim 1, wherein the controller-transmitter and the sound-speech processor communicate using a direct wired connection.

11. A system as in claim 1, wherein the receiver-stimulator consists essentially of an ultrasound transducer which generates a stimulation signal in response to the acoustic energy transmitted by the controller-transmitter, circuitry which rectifies the stimulation signal, and at least one stimulation electrode which delivers the rectified signal to the cochlea.

* * * * *